(12) United States Patent
Law et al.

(10) Patent No.: US 8,495,999 B2
(45) Date of Patent: Jul. 30, 2013

(54) AIRWAY INTUBATION DEVICE

(76) Inventors: John Adam Law, Halifax (CA);
Michael Gross, Halifax (CA); George James Kovacs, Halifax (CA); Steve Carkner, Ottawa (CA)

(*) Notice: Subject to any disclaimer, the term of this patent is extended or adjusted under 35 U.S.C. 154(b) by 1026 days.

(21) Appl. No.: 12/047,264

(22) Filed: Mar. 12, 2008

(65) Prior Publication Data

US 2009/0032016 A1 Feb. 5, 2009

Related U.S. Application Data

(60) Provisional application No. 60/953,992, filed on Aug. 4, 2007.

(51) Int. Cl.
*A61M 16/00* (2006.01)
*A61B 1/00* (2006.01)
*A61B 1/04* (2006.01)
*A61B 1/267* (2006.01)

(52) U.S. Cl.
USPC ....... 128/200.26; 600/194; 600/120; 600/109

(58) Field of Classification Search
USPC ............ 128/200.24, 200.26, 207.14, 207.15; 600/131, 109–112, 120, 184–200
See application file for complete search history.

(56) References Cited

U.S. PATENT DOCUMENTS

| | | | | |
|---|---|---|---|---|
| 4,211,234 A | * | 7/1980 | Fisher | 128/200.26 |
| 4,306,547 A | * | 12/1981 | Lowell | 600/188 |
| 4,384,570 A | * | 5/1983 | Roberts | 600/187 |
| 4,846,153 A | * | 7/1989 | Berci | 600/109 |
| 4,982,729 A | * | 1/1991 | Wu | 600/187 |
| 5,243,399 A | * | 9/1993 | Koop et al. | 356/153 |
| 5,261,392 A | * | 11/1993 | Wu | 600/188 |
| 5,377,668 A | * | 1/1995 | Ehmsen et al. | 600/121 |
| 5,655,528 A | * | 8/1997 | Pagan | 128/207.14 |
| 6,142,144 A | | 11/2000 | Pacey | |
| 6,543,447 B2 | | 4/2003 | Pacey | |
| 6,655,377 B2 | | 12/2003 | Pacey | |
| 6,672,305 B2 | * | 1/2004 | Parker | 128/200.26 |
| 6,843,769 B1 | | 1/2005 | Gandarias | |
| 6,901,928 B2 | * | 6/2005 | Loubser | 128/200.26 |
| 6,962,563 B2 | * | 11/2005 | Yasunaga | 600/114 |
| 7,156,091 B2 | | 1/2007 | Koyama | |
| 7,214,183 B2 | * | 5/2007 | Miyake | 600/131 |
| 8,022,979 B2 | * | 9/2011 | Miyamoto et al. | 348/65 |
| 2005/0256375 A1 | * | 11/2005 | Freed | 600/146 |
| 2006/0020171 A1 | * | 1/2006 | Gilreath | 600/188 |
| 2007/0106117 A1 | | 5/2007 | Yokota | |
| 2007/0106121 A1 | | 5/2007 | Yokota | |
| 2007/0106122 A1 | | 5/2007 | Yokota | |
| 2007/0167686 A1 | | 7/2007 | McGrath | |
| 2008/0230054 A1 | * | 9/2008 | Prineas | 128/200.26 |

* cited by examiner

*Primary Examiner* — Justine Yu
*Assistant Examiner* — Valerie L Skorupa
(74) *Attorney, Agent, or Firm* — Gordon Thomson

(57) ABSTRACT

An airway intubation device having a one-piece molded body of biocompatible material with an ergonomically designed hand piece for left hand manipulation. The body includes a cap piece and linear-curved-linear insertion piece having a channel in one side thereof for insertion of an endotracheal tube. The channel has a wide entry portal disposed ahead of the hand piece so that a clinician may load the channel with a tube while the insertion piece is in the mouth of the patient without having to view the entry portal. The device includes illumination means and viewing means comprising an eye piece or a video display unit mounted to the cap piece so that a clinician can view the insertion of the tube between the vocal cords of a patient without contact.

1 Claim, 20 Drawing Sheets

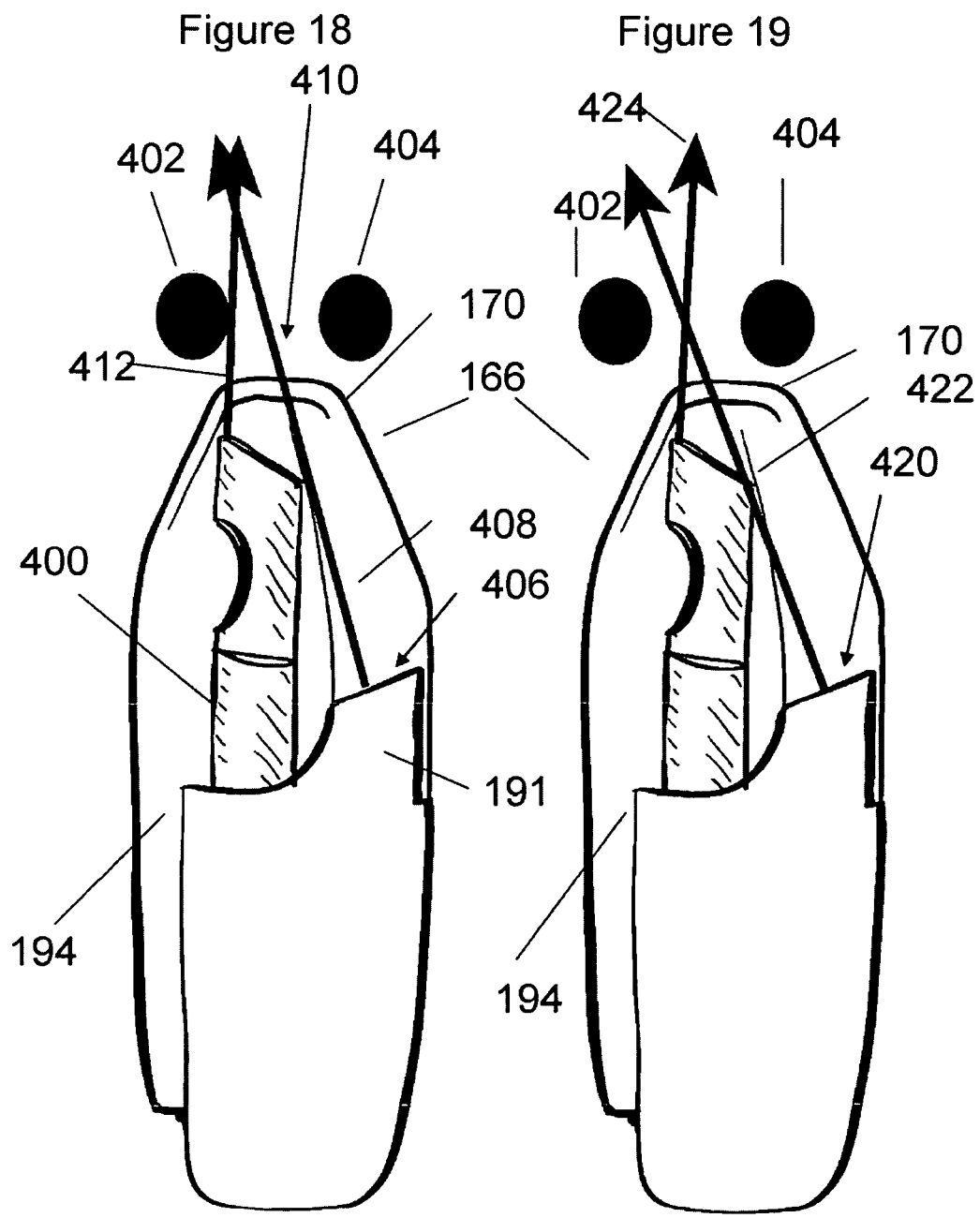

AIRWAY INTUBATION DEVICE

RELATED APPLICATIONS

This application claims the benefit of provisional patent application No. 60/953,992 filed in the United States Patent and Trademark Office on Aug. 4, 2007.

BACKGROUND OF THE INVENTION

1. Field of the Invention

This invention relates to medical devices and more specifically to an improved airway intubation device.

2. Background of the Invention—the Problem to be Solved

In both acute-care medicine and as part of delivering a general anesthetic for an operative procedure it is often necessary to insert a breathing tube into the airway of a living organism, most often a human, but in some cases this can also apply to pets, livestock and other animals. This procedure is called endotracheal intubation. A variety of tools exist for performing this procedure, which is usually performed by highly trained professionals in a hospital, or pre-hospital setting. Most intubations are performed with direct laryngoscopy, using a device called a direct laryngoscope, which incorporates a curved or straight blade. The laryngoscope is inserted into the patient's mouth and throat by the clinician who is generally standing at the patient's head. The laryngoscope blade controls the tongue and other internal structures to help directly visualize the vocal cords (glottic inlet). The vocal cords mark the entry point to the wind pipe (trachea) and lungs and represent the target destination through which the breathing tube (endotracheal tube) is advanced.

When intubating a human, the goal is to place an endotracheal tube between the vocal cords (the glottic inlet) into the upper trachea to allow oxygen to be supplied to the lungs. It is preferable that the vocal cords be seen during intubation as they are the best guide to entry into the trachea and lungs, as opposed to incorrect entry to the esophagus and stomach. Unrecognized failure to correctly place an endotracheal tube into the trachea can result in a failure of oxygenation, and the patient's death.

In expert hands, endotracheal intubation using a direct laryngoscope will be easy 95% of the time. A real challenge remains in that it takes 50 or more intubations to achieve a 90% success rate. In an attempt to deal with this learning curve issue and to help manage difficult cases, so-called 'alternative intubation' devices have been developed. Some such scopes feature an "L"-shaped blade and use fiber- or video-optics for visualization. Using these devices, visualization of the vocal cords is often made easier but actual delivery of the breathing tube (endotracheal tube, ETT) between the cords into the windpipe (trachea) of the patient often remains difficult. When using these devices, not infrequently, during navigation of the ETT to and through the vocal cords, forward advancement of the ETT can be impeded by 'hang-up' on the right vocal cord. In addition, sporadic cases of trauma to the soft palate have been reported.

In another prior art device, a rounded tubular "J"-shaped blade was used incorporating a tube delivery channel to help with tube delivery. However, while the delivery channel was an attempt to deal with the challenges of tube placement, success was often impaired because: (a) the rounded (tubular) blade was too narrow to control the tongue and soft tissues well, so that one could often 'get lost' and not see the target vocal cords, and (b) the tube emerged from the delivery channel heading in an angle that often resulted in the tube being directed incorrectly into the esophagus and not the trachea.

There is a continued need for an intubation device for use by clinicians that is highly reliable, relatively easy to use and is able to link visualization of vocal cords directly with endotracheal tube placement.

SUMMARY OF THE INVENTION

Our invention is an airway intubation device comprising a cap piece, a hand piece and an insertion piece molded into a single rigid body from a suitable biocompatible material. The hand piece is ergonomically adapted for left hand manipulation and comprises a first end, a second end, a vertical axis, an oval cross-section for hand clasping, a finger contact portion, a palm contact portion and a thumb contact portion permitting fine control to be exerted on the device with minimum force. The finger contact portion comprises a train of alternating ridges and valleys adapted for placement between a clinician's index, middle, ring and small fingers for even force distribution. The palm contact portion is adapted for full contact with a clinician's palm so that manipulative forces can be transmitted to the device through the entire surface of the clinician's palm. The thumb contact portion is adapted for contact with the side of the clinician's thumb so that manipulative forces can be exerted on the thumb contact portion.

The insertion piece comprises, from top to bottom, a first linear portion having a first axis, contiguous with a curved portion, contiguous with a second linear portion having a second axis. The first axis is inclined in a positive direction from the vertical axis. The second axis and the vertical axis intersect at a first predetermined angle which is between 91 degrees and 120 degrees and preferably about 107 degrees.

The second linear portion comprises a truncated tip, a top surface, a bottom surface and a flange member extending around the truncated tip to avoid tissue damage during intubation. The top surface of the insertion piece has a centre-line and a raised element disposed along and over the centre-line for helping to situate the blade in a midline position during intubation by frictional contact with the median sulcus (of the tongue). The first axis and the second axis form a second predetermined angle between 80 and 89 degrees and preferably about 85 degrees.

The device is molded from a suitable biocompatible material designed for translucence so that light is able to disperse through it. This improves illumination of the intubation operation and guidance of the insertion piece into the trachea of the patient. The device can also be fabricated from other materials such as stainless steel.

Within the insertion piece there is an open endotracheal tube channel having a wide entry portal and an exit portal. The channel has a tubular-shaped cross-section providing at least 200 degrees of circumferential coverage for an inserted endotracheal tube. The entry portal is wider than the endotracheal tube to aid ease of entry of the ETT into the channel during intubation. The open slot to the channel, which runs it full length, is designed to be narrower than the outer diameter of the ETT, to ensure the ETT remains within the channel during advancement.

The airway intubation device includes an illumination system and an image viewing system with an image gathering component permitting the clinician to view insertion of an endotracheal tube into a patient's trachea. The illumination system comprises at least one LED lamp disposed adjacent to the exit portal for illuminating the patient's vocal cords and surrounding areas. In another example the illumination system comprises an LED lamp located within the hand piece with light being transmitted through the insertion piece using fiberoptic bundles (light guide) to a portal adjacent to the image viewing system. The image viewing system may be a viewing piece (eyepiece) on the cap piece connected by fiberoptic cable (image gathering component) to a viewing portal adjacent to the exit portal. In another example, the image gathering component of the viewing system may be a camera adjacent to the exit portal connected to a video display screen attached to the cap piece.

The focal path of the image gathering system is designed to guide the endotracheal tube through the centre of the vocal cords.

In one example of the invention, the video display includes an anatomically correct aiming reticle representing the vocal cords so that the clinician can guide the tube between the cords while viewing the video display screen.

BRIEF DESCRIPTION OF THE DRAWINGS

FIG. 18 and FIG. 19 illustrate the aiming offset of one example of the invention (FIG. 19) compared to a prior art device (FIG. 18).

DETAILED DESCRIPTIONS OF EXAMPLES OF THE INVENTION

Figure 1:
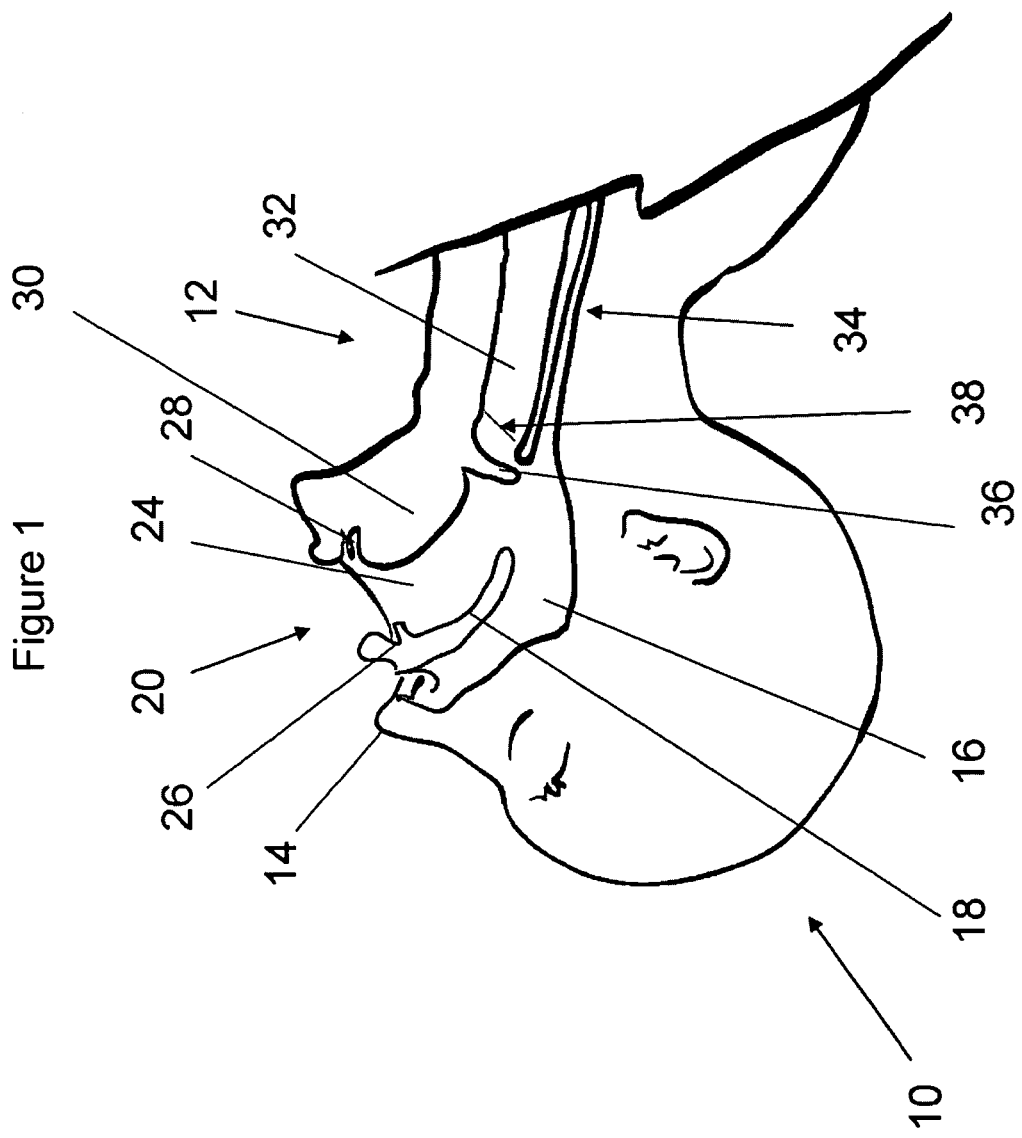
FIG. 1 is a side view of the head and neck of a patient showing parts relevant to intubation.

The process and principals of endotracheal intubation are well known. Referring to FIG. 1, there is shown a cross-section of a human head (10) and neck (12) to illustrate the anatomy relevant to intubation. There is shown the nose (14) and nasal passage (16). The palate (18) separates the mouth (20) and oral cavity (24) from the nasal passages. The upper (26) and lower (28) teeth and tongue (30) are also shown. During breathing, air travels down the windpipe or trachea (32) into the lungs. Food and water travel down the esophagus (34) to the stomach. To avoid choking, the epiglottis (36) closes the trachea when swallowing and opens again to permit breathing. The vocal cords (38) are located below the epiglottis and mark the entry point into the trachea. All of these airway soft-tissues are vulnerable to damage during intubation. The major challenge in performing endotracheal intubation relates to the need to see around the corner created in part by the tongue and epiglottis. The tongue and the epiglottis must be engaged with some force to manipulate and control both. With most intubation devices, during intubation, the tongue must be compressed out of the way and the epiglottis must be lifted to expose the vocal cords, through which the endotracheal tube is placed into the trachea.

Figure 2:
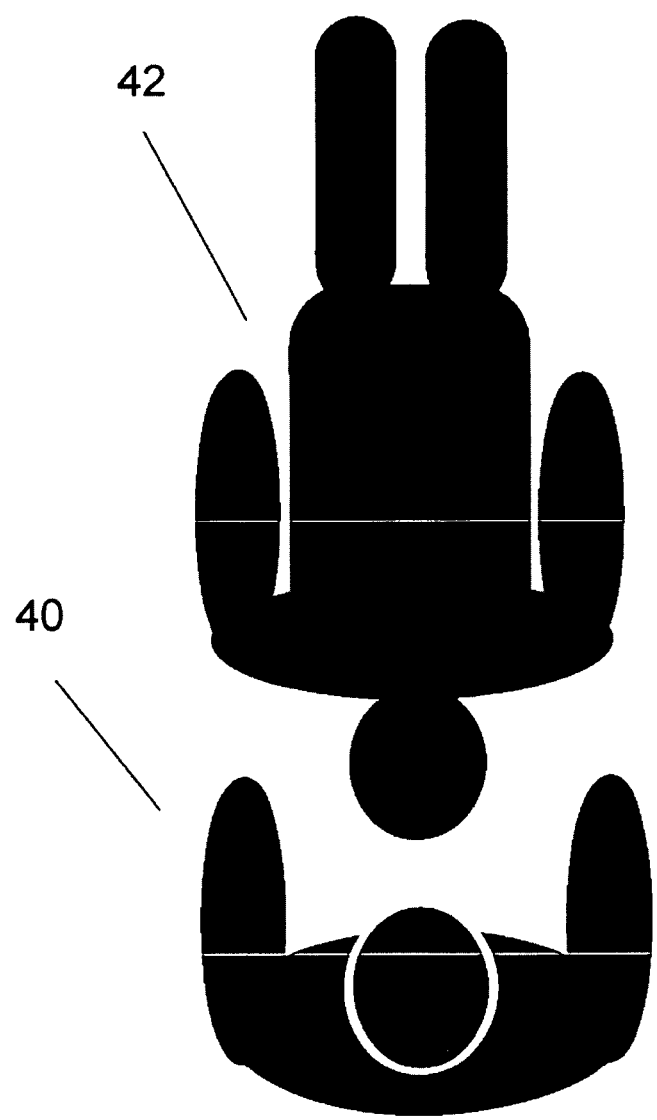
FIG. 2 is a top view showing placement of a clinician relative to a patient during intubation.

Referring to FIG. 2, during the intubation process, the clinician (40) is located at the head of the patient (42). Throughout this specification I will use the term "clinician" to mean any medical care giver authorized to perform tracheal intubation.

Figure 3:
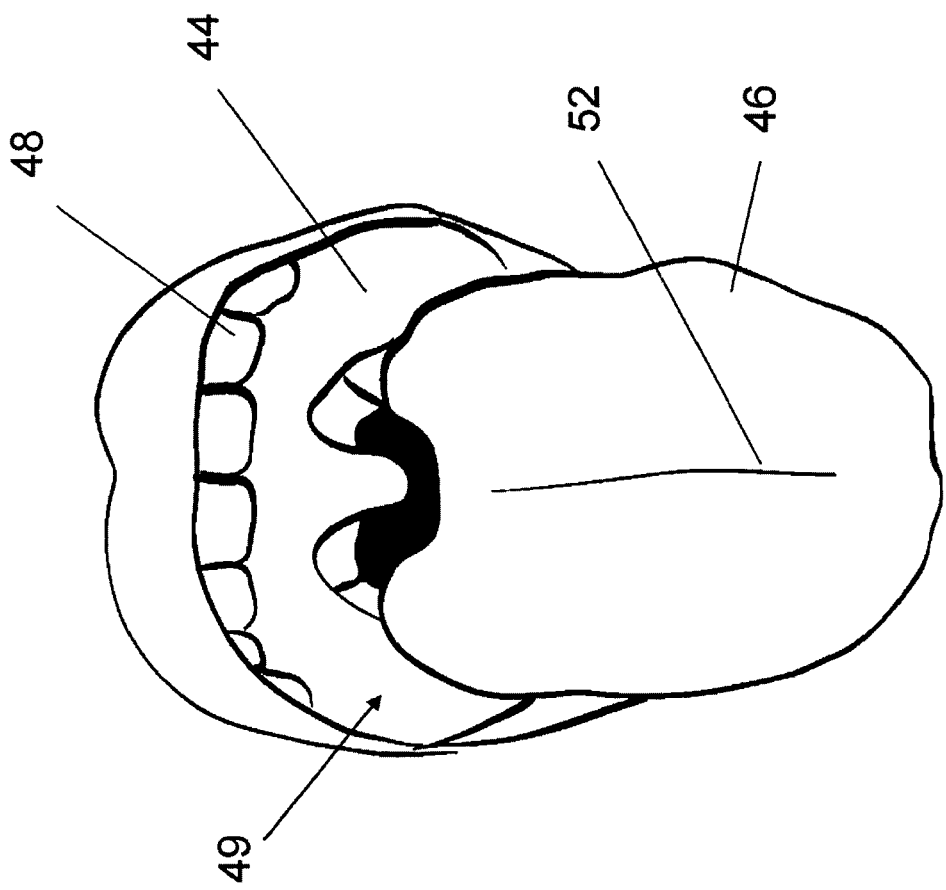
FIG. 3 is a view of a patient's mouth as viewed by a clinician showing parts relevant to intubation.

Endotracheal intubation may be required as part general anesthesia for an operative procedure or as part of resuscitative efforts in managing acutely ill patients. Regardless of the indication, there is a need for an intubation device that is easy to use and permits accurate intubation without damaging the parts of the mouth or throat. Referring to FIG. 3, the clinician views the mouth (44) of the patient from an upside-down perspective. The tongue (46) must be controlled, the mouth may be closed, teeth (48) may block entry into the oral cavity (49) and can be damaged with instrumentation. An anatomical feature of the tongue which will be referred to later in this document is the mid-line groove (52) or median sulcus.

Figure 4:
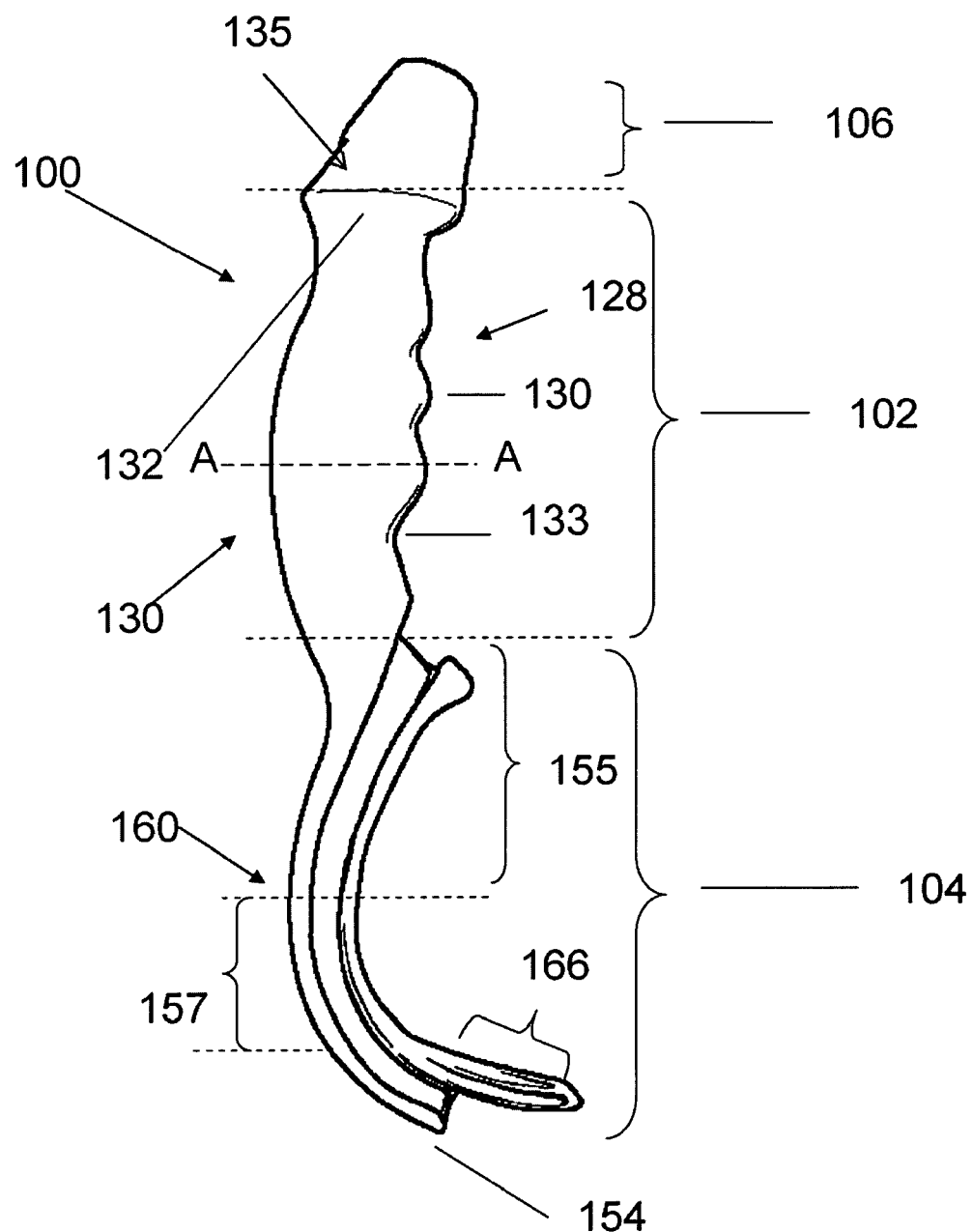
FIG. 4 is a right side view of one example of the invention.

Referring now to FIG. 4, there is shown a side view of the invention which is an airway intubation device (100) comprising a hand piece (102), an insertion piece (104) and a cap piece (106). In one version, the cap piece, hand piece and the insertion piece comprise a rigid single molded body. The body is molded from a suitable durable biocompatible material.

Figure 5:
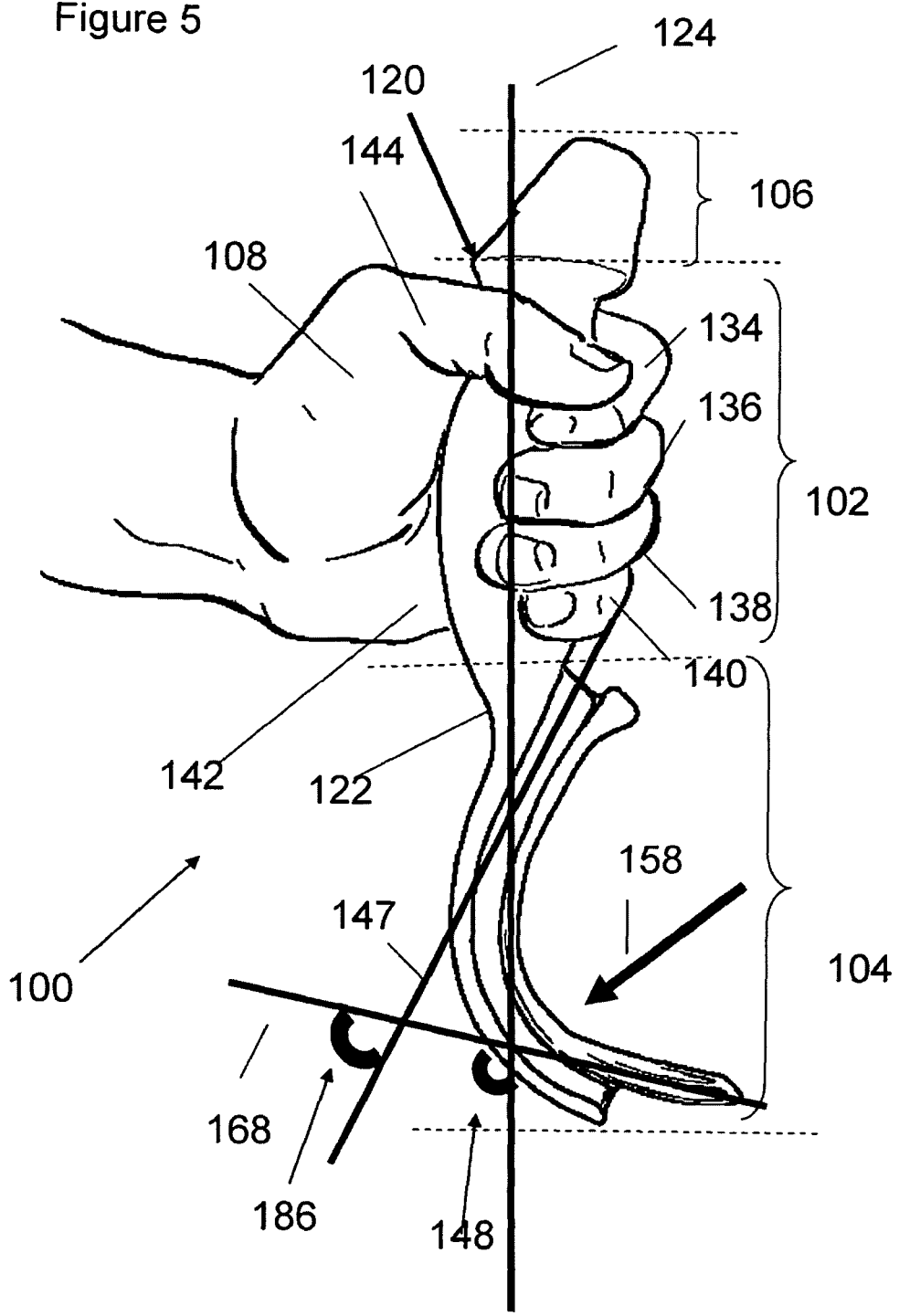
FIG. 5 is a right side view of one example of the invention in a left hand grasp.

Referring to FIG. 5 which is a side view of the device (100) grasped by a left hand (108) the device (100) is adapted for single left hand (108) manipulation.

Figure 6:
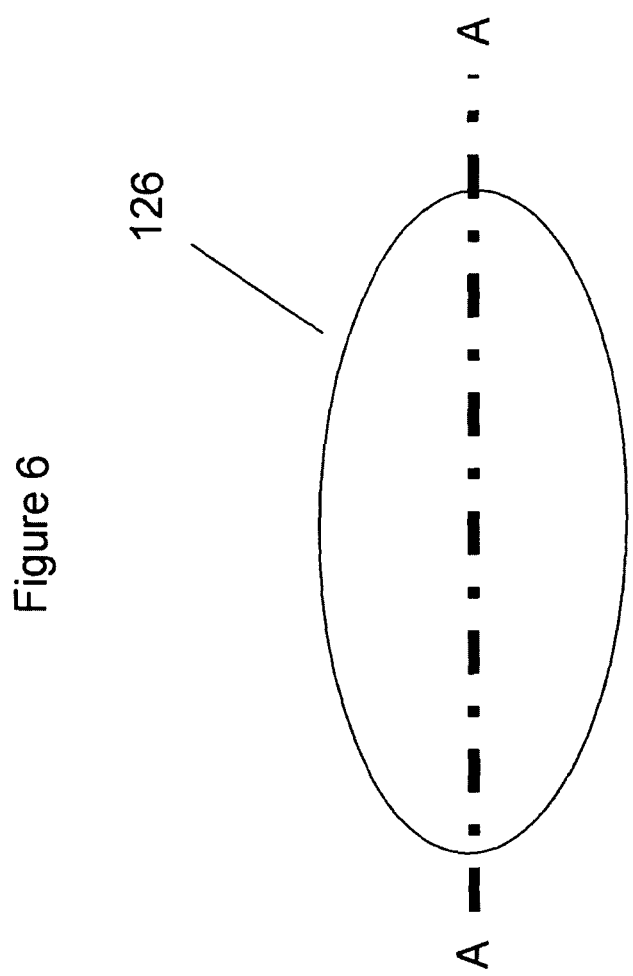
FIG. 6 is a cross-section of the hand piece of one example of the invention.

Referring to FIGS. 4, 5 and 6 the hand piece (102) comprises a first end (120) and a second end (122), an axis (124) and an oval cross-section (126) (FIG. 4, Section A-A). The hand piece, as illustrated in FIG. 4, is adapted for clasping and so further comprises a finger contact portion (128), a palm contact portion (130) and a thumb contact portion (132). The hand piece permits fine manipulation control of the device in a forward-backward, side-to-side and rotational direction about axis (124) during an intubation process.

The device (100) finger contact portion (128) comprises a train of alternating ridges (130) and valleys (133). The ridges (130) are adapted for placement between the index (134), middle (136), ring (138) and small finger (140) respectively for even distribution of force exerted by the hand (108) on the hand piece (102) for manipulation with minimum force. The palm contact portion (130) is adapted for full palm (142) contact so that manipulative forces can be transmitted to the device through the entire surface of the hand (108). The thumb contact portion (132) is adapted for contact with the side of the thumb (144) so that side-to-side forces can be exerted on the pad for maneuvering the device. The hand piece is designed for optimal biocompatibility with a wide variety of human hands. Above the thumb contact portion (132) is a ridge (135) that is adapted to prevent the hand from slipping from the hand piece when the device is being lifted in a vertical direction.

The vertical axis of the hand piece (124) and the first axis (168) of the second linear portion (166) of insertion piece (104) form a predetermined angle (148) so that during insertion of the insertion piece into the throat of the patient the insertion piece will position itself beneath the epiglottis and permit a well controlled upwards lifting motion on the handle piece (102). Angle (148) is preferably 107 degrees but can range between 91 and 120 degrees. Angle (148) also ensures that the handle piece will not strike the chest of the patient during intubation.

Figure 7:
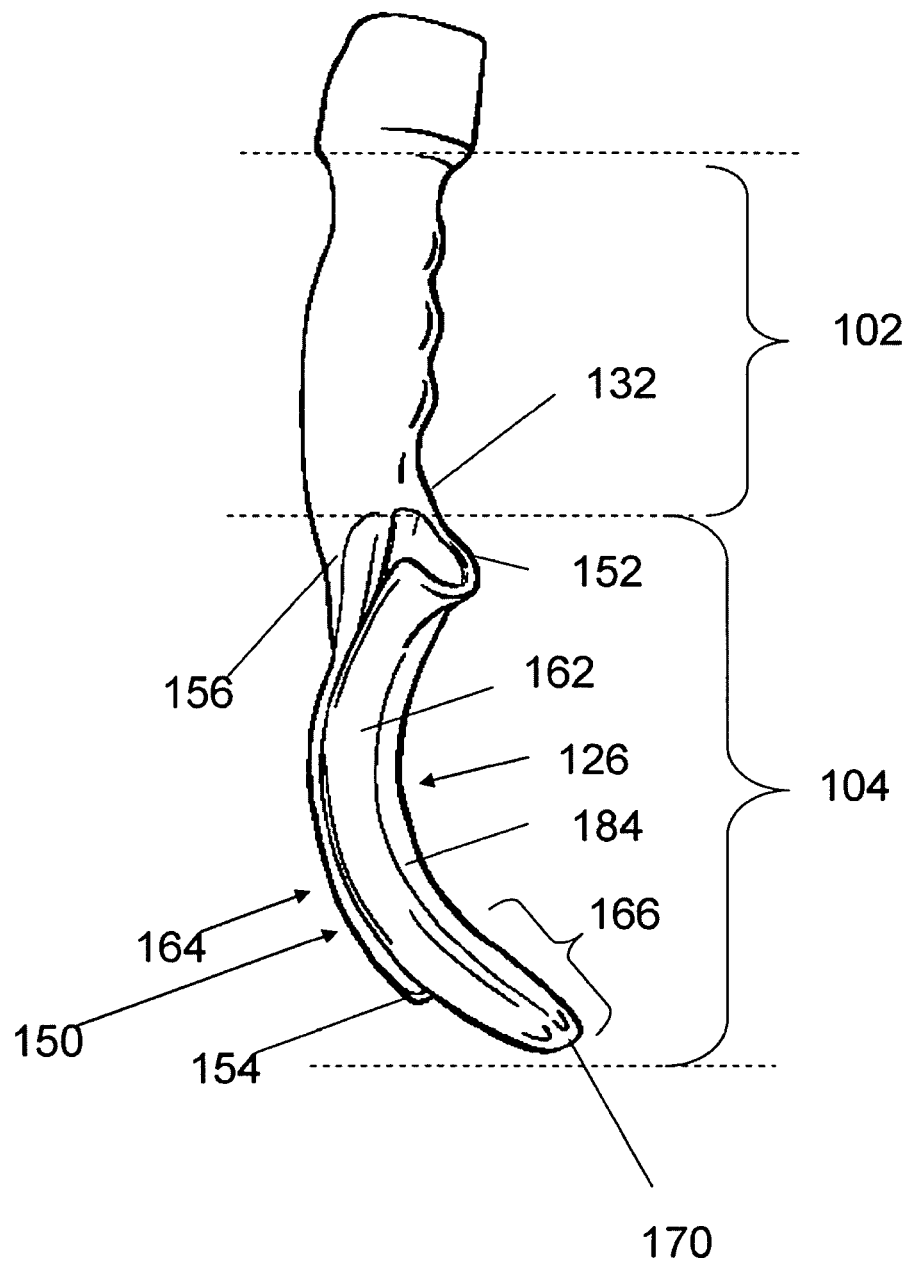
FIG. 7 is a front perspective view of one example of the invention.
Figure 8:
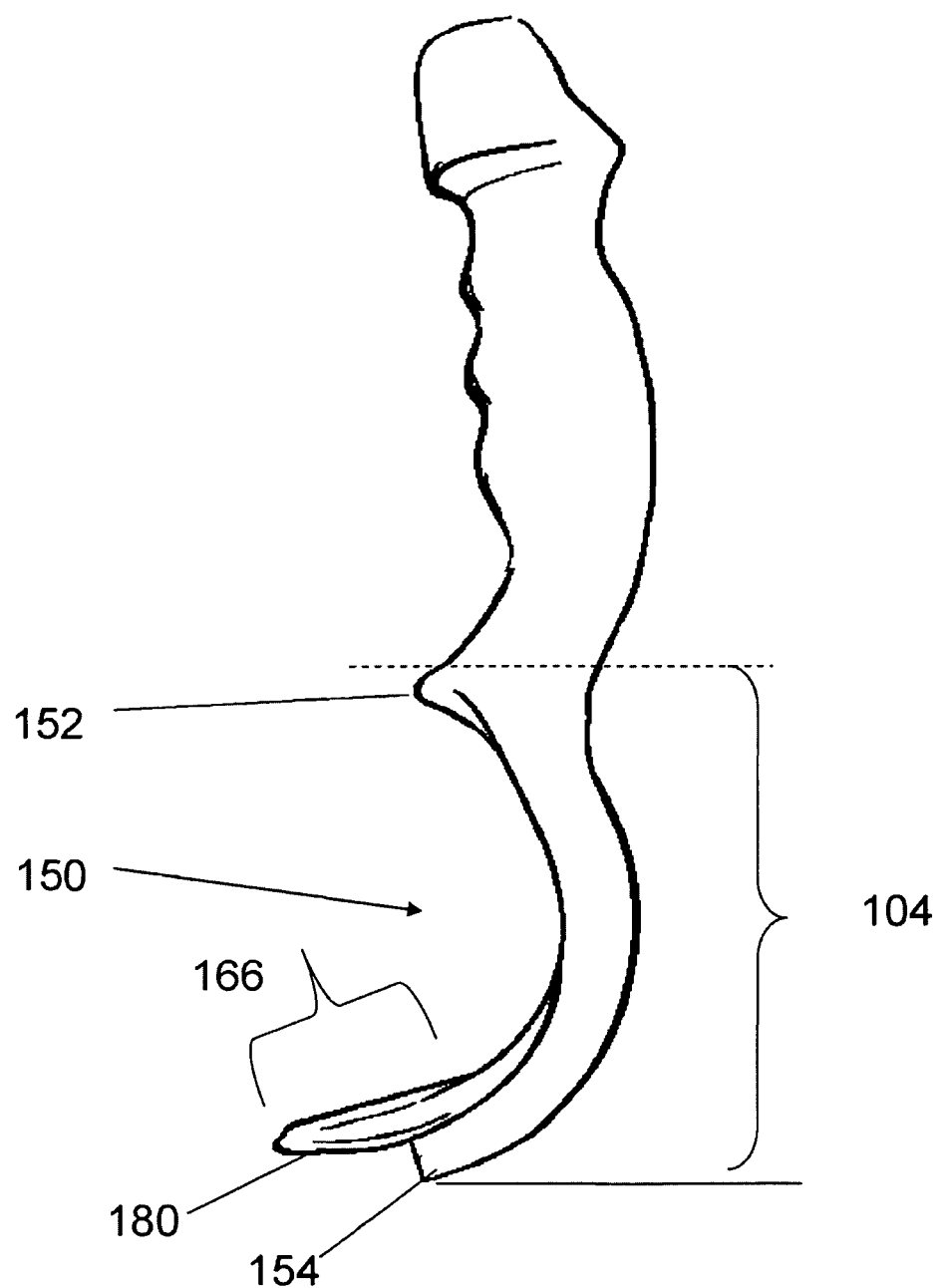
FIG. 8 is a left side view of one example of the invention.

Referring now to FIG. 4 and FIG. 5 (right hand views), FIG. 7 (perspective view) and FIG. 8 (left hand view) insertion piece (104) comprises a linear-curved-linear member (150) having a first end (152) and a truncated tip (170). The first end (152) further includes a side part (156) that is integral to second end (132) of the hand piece (102). The linear-curved-linear member (150) comprises a first linear portion (155), a curved portion (157) and a second linear portion (166). The first linear portion (155) has an axis (147) that has a positive inclination from the vertical axis of the hand piece. The curved part has a predetermined radius (158) adapted for optimum positioning of the ETT as it emerges from the delivery channel. The radius can vary but it is at least 3 cm. The curved part can have a single radius or can be a curve with varying radii. The first linear portion (155) extends from the first end (152) to approximately mid-way (160) along the linear-curved-linear member (150). The curved portion (157) extends from approximately mid-way (160) to wherein the second linear portion (166) commences.

Figure 9:
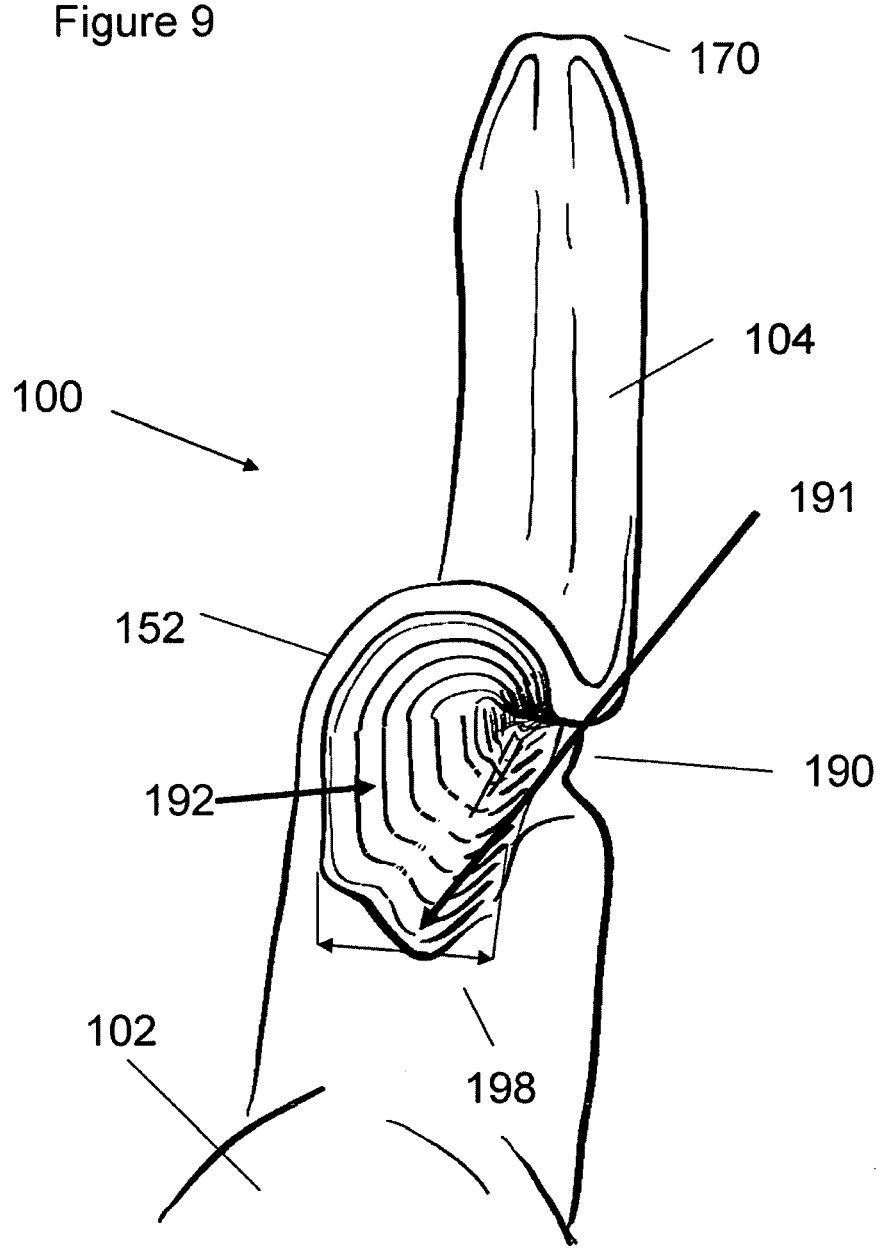
FIG. 9 is a top view of the insertion piece of one example of the invention.

Referring to FIG. 9, there is shown a top view of the insertion piece (104) of the device (100). The insertion piece is located below the hand piece (102) and commences at end (152) forward of the second end of the hand piece. The insertion piece has a first end (152) and a tip (170). A tubular-shaped channel (190) runs the length of the insertion piece from first end (152) to second end (154—See FIG. 7 and FIG. 8). In this figure it is the right side but it can also be the left side. The channel has a funnel shaped entry portal (192) for easy insertion of an endotracheal tube as more fully described below. The width (198) of the entry portal (192) is much wider than the tube for easy entry and then narrows to a width that is slightly narrower than the tube so that tube does not prematurely disengage from the channel during intubation. Control of the tube is always maintained by the clinician.

Figure 10:
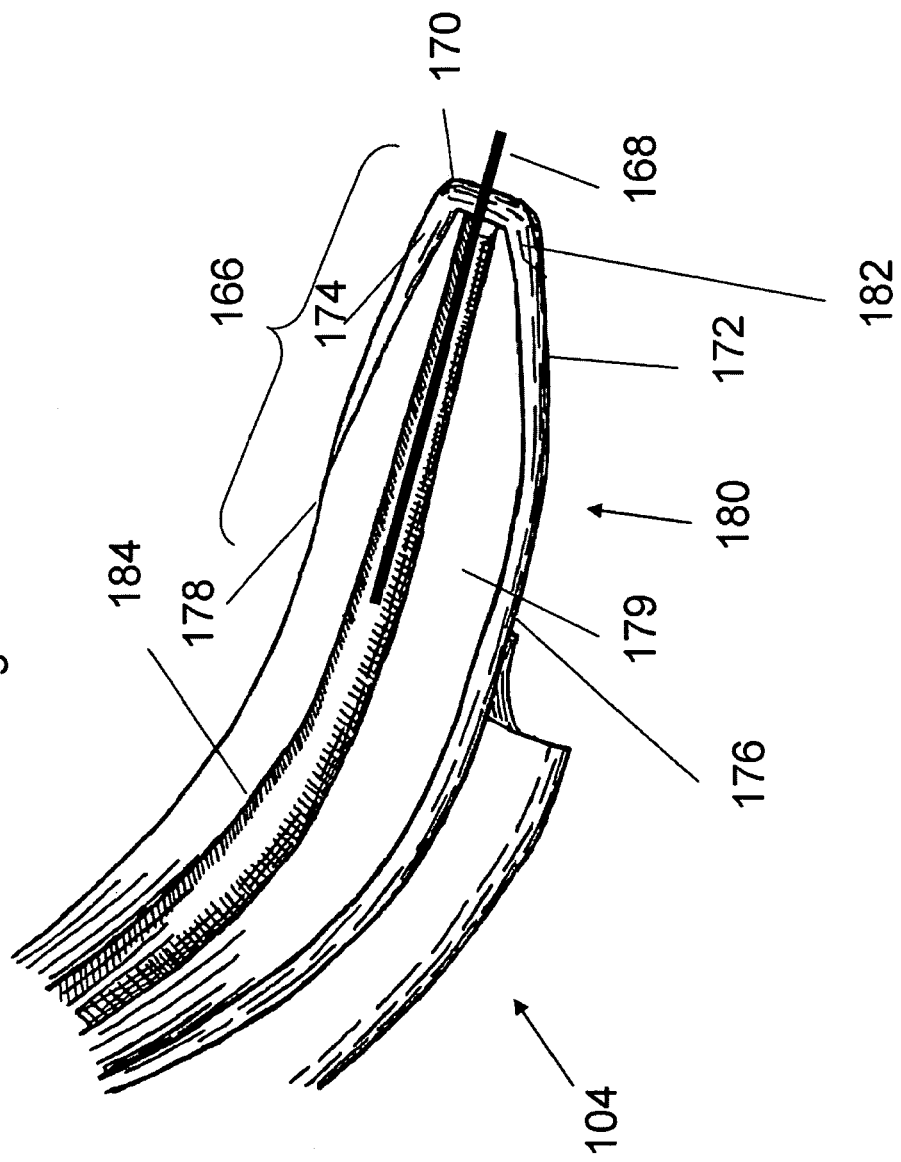
FIG. 10 is an enlarged view of the second linear segment of the insertion piece of one example of the invention.

Referring now to FIGS. 7 to 10 where FIG. 10 is an enlarged view of the second linear portion (166) of the insertion piece (104). The insertion piece (104) further comprises a top surface (162) and a bottom surface (164). Portion (166) of the linear-curved-linear insertion device (104) extends from end of the curved portion (157 FIG. 4) to tip (170). Portion (166) has an axis (168), a front truncated tip (170), a first inwardly angled side edge (172), a second opposite inwardly angled side edge (174), a third side edge (176) and fourth parallel opposite side edge (178). Portion (166) also comprises a top surface (179), a bottom surface (180) and a flange (182) extending around the front truncated edge (170) and the inwardly angled first (172) and second (174) edges. The flange (182) is rounded and adapted to blunt the tip of portion (166) to avoid tissue damage during intubation. The flange also forms an area of higher pressure against the epiglottis and soft tissue in the area of the epiglottis when the insertion piece is lifted to expose the vocal cords. This increased pressure helps provide traction on the epiglottis and ensures that the epiglottis is held in place thus reducing the tendency for the epiglottis to slide off the second linear portion, as may be the case with flat bladed intubation devices. The problem is especially true when the insertion piece is constructed from smooth stainless steel. The flange may optionally include textures which further enhance the grip and control afforded by this feature. The top surface (162) of the insertion piece (104) including the top surface (179) of the second linear portion (166) are contiguous and comprise a raised element (184) located along the centre-line (168). The raised element is adapted for stabilization of the device in the midline of the patient's tongue during intubation by engaging the mid-line groove of the tongue (median sulcus Item 52 FIG. 3) in a frictional manner. The raised element may also be textured to improve its frictional gripping action on the tongue.

Referring to FIG. 5, the axis (168) of the second linear portion (166) and the axis (147) of the first linear portion (155) intersect at a second predetermined angle (186). Angle (186) is between 80 and 89 degrees. In one example of the device, the predetermined angle (186) is about 85 degrees. Generally, it is important that the second linear portion of the insertion piece forms a slightly obtuse angle with the first linear portion of the insertion piece in order to achieve proper epiglottis lift and to help direct the tube through the vocal cords and down the trachea. Maintaining this range of angles also ensures that tip (170) of the insertion piece (104) will pass beneath the epiglottis of the patient during intubation and facilitate epiglottis lift for accurate guidance of the endotracheal tube between the vocal cords of the patient. Portion (166) is preferably 3 cm long but can range from 2 cm to 7 cm in length.

Figure 11:
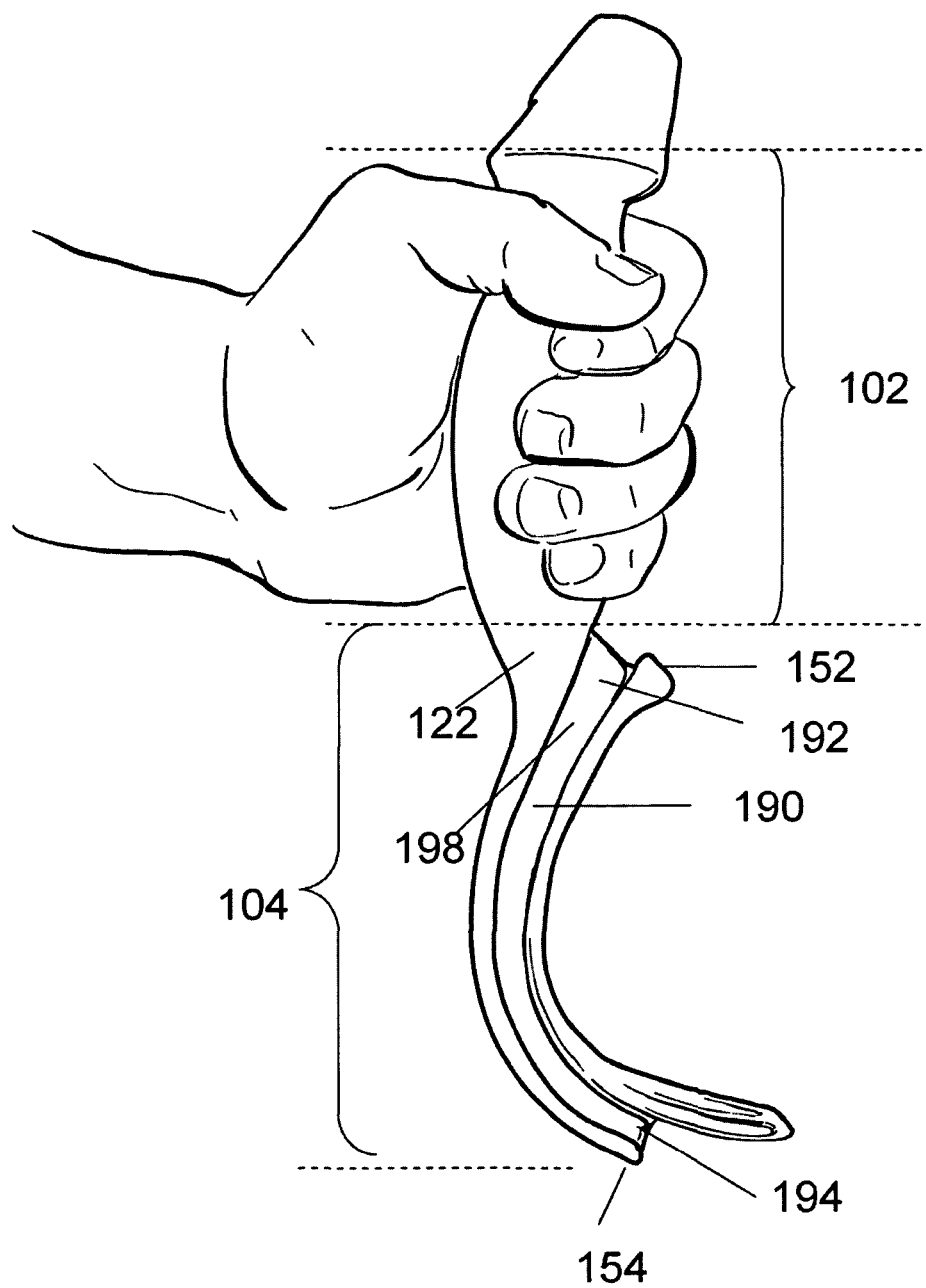
FIG. 11 is the same view as FIG. 5.
Figure 12:
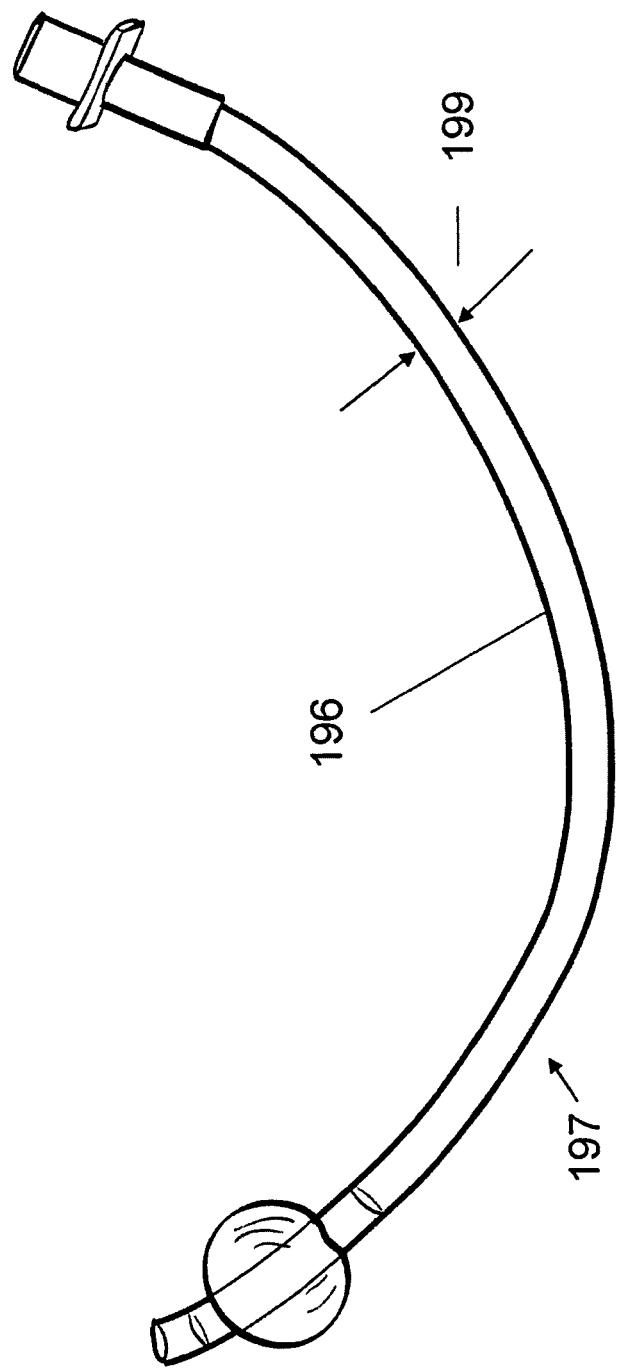
FIG. 12 is a view of an endotracheal tube of the type used with all examples of the invention.

Referring now to FIG. 9 and FIG. 11, which is the same as FIG. 5, the insertion piece (104) includes an open channel (190) located along one side extending from a first end (152) to a second end (154). The open channel has a tubular-shaped cross-section so that it will cover at least 200 degrees of an endotracheal tube inserted into it. The open channel (190) has an entry portal (192) located at the first end and an exit portal (194) located at the second end for passage of an endotracheal tube (196) as illustrated in FIG. 12. The entry portal (192) is disposed ahead of the handle piece (102) second end (122) for easy ETT insertion. The entry portal has a flared width (198) larger than the width (199) of the endotracheal tube for easy tube insertion. A small groove (191) about 1 mm deep is located on the lower surface of the open channel from the entry portal to the exit portal extending throughout the channel of the insertion piece. Most endotracheal tubes have a small ridge (197) on their outer convex side. This groove (191) is meant to accommodate a slight ridge line (197) often found on the outer contour of the many tubes. The ridge line on the tube functions as a radio-opaque strip, so that it shows up on x-rays. In this example of our invention it allows further stabilization of the endotracheal tube within the channel. The exit portal (194) is located at end (154) below portion (166). The diameter of the open portion of the delivery channel (190) is slightly less than that of the endotracheal tube throughout its length to ensure that the tube remains within the channel during advancement. The motion of the tube through the channel of the insertion piece is guided by the clinician's free hand, and following its correct placement, is disengaged from the open portion of the channel by the clinician's pinching the tube and pulling it away from the channel, to the right.

The entry portal (192) of channel (190) acts as a 'tube collection area'. The reasoning behind this is that with traditional direct laryngoscopy, the clinician first places the scope in the patient, gets the view, and then as the next maneuver, picks up the tube and passes it into the patient's trachea. In this example of our invention, the wide collection area is unique and is designed to similarly enable the clinician to first place the device in to the patient, then place the tube via the wide collection area, without taking his or her eyes off the view of the vocal cords. Other competing scopes require prior loading of the tube.

A groove (150) is continuous with the channel of the insertion piece and is adapted to provide additional guidance to the tube as it emerges from the channel (190) and maintains the tube in a straight orientation for insertion between the patient's vocal cords. This groove (150) is disposed on the underside (152) of portion (166) and is tapered from its rear (154) to its front (156). In one example of the invention the illumination system uses a light guide (126 or 132) to transmit light from an LED lamp located within the hand piece to illuminate the interior of the throat once the insertion piece is inserted. In another example of the invention there may be two LED lamps (126 and 132) that provide direct illumination and are located on the right side of the exit portal (194). The image gathering component (148) of the image viewing system is further explained below. The terminal components (148,126,132) of these systems (illumination and image viewing) may vary slightly in location but are grouped together within a 10 mm radius and may be on either side of the exit portal. As further described below, these components are connected to their respective power sources and controllers by a bore (See FIG. 15 Item 224) that runs the length of the insertion piece and into the hand piece. The bore can be easily molded into the insertion piece and the hand piece of the body. Although a single piece body is preferred for ease of manufacture and less cost, a multiple piece mold can be used to accommodate the various bores, inserts and battery magazines illustrated herein. As well, the close proximity of the one or two lamps to the viewing lens (148) assists in keeping the lens free of fog and moisture while in the throat of the patient. The lamps emit sufficient heat to act as a defogging device for the viewing lens. When the insertion device is made from a suitable thermoplastic material having translucent properties, the illumination emitted by the LED devices is able to disperse through the insertion device providing better illumination of the trachea of the patient on both sides of the insertion device and permitting more accurate guidance of the tube between the vocal cords.

Figure 14:
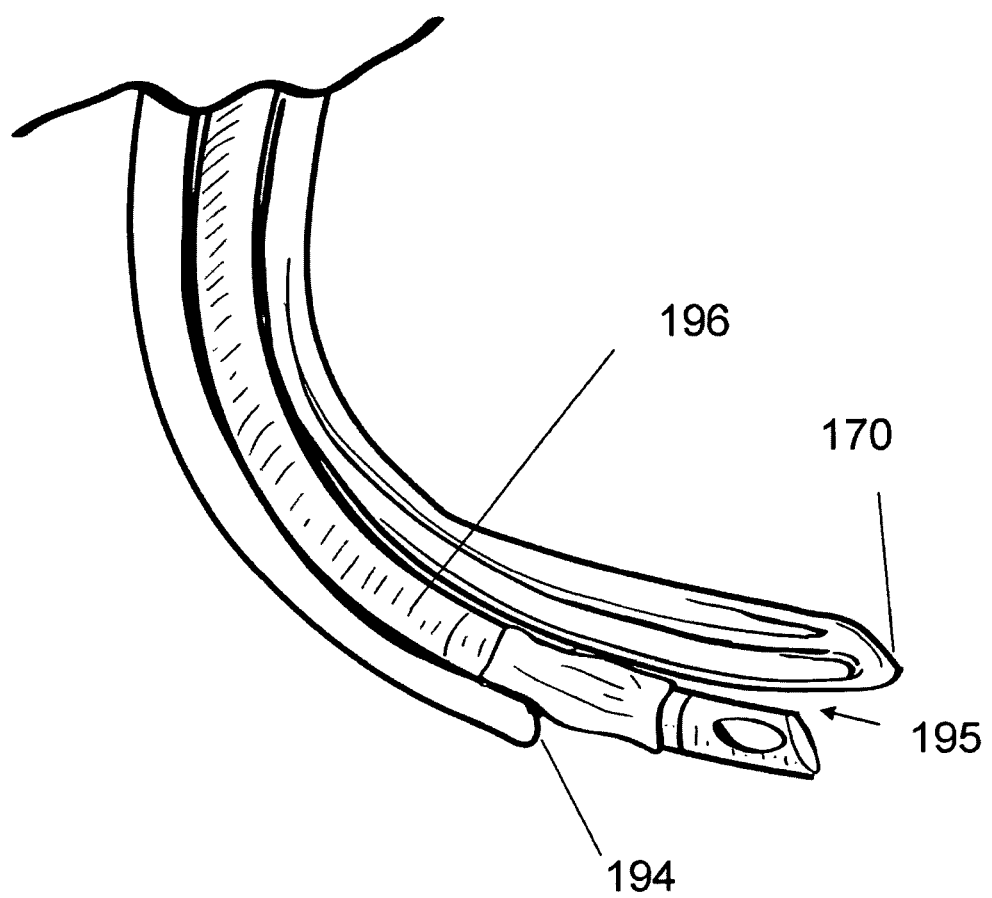
FIG. 14 is a cross-sectional view of an endotracheal tube exiting the channel of one example of the invention.

Referring to FIG. 14, there is illustrated a side view of the endotracheal tube (196) as it emerges from the second end (194) of the open channel (190). The curve of the insertion piece, the diameter of the open channel and other dimensional constraints ensure that the tube exits the channel with a small gap (195) between the tube and the tip (170) of portion (166). This width of the gap (195) should be between 2 millimeters and 10 millimeters. If the gap is too small, the tube may catch on the upper portion/anterior commissure of the vocal cords. If the blade tip is positioned above the epiglottis in the vallecula, the tube may impact and down-fold the epiglottis resulting in a failed intubation. If the gap is too large the tube may drop below the vocal cords and enter the esophagus resulting in air being delivered into the stomach instead of the lungs. The interior geometry of the channel of the insertion piece creates a '3-point fixation', whereby there are 3 points of contact between the tube and the inside the curvature of the channel of the insertion piece blade. The 3-point fixation dictates how the advancing tube exits the channel, thus how far away from the tip of the insertion piece it will be.

Figure 15:
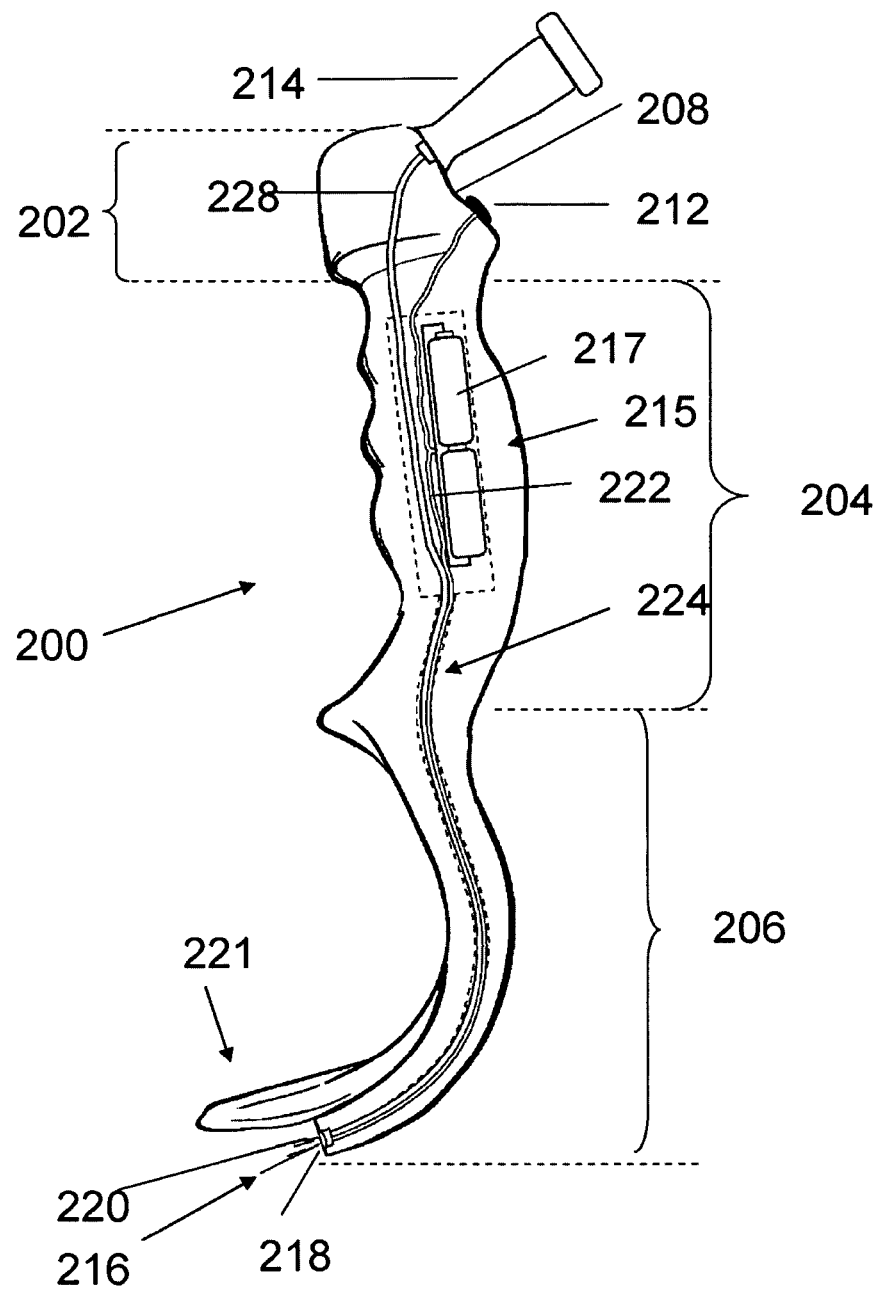
FIG. 15 illustrates a side view of one example of the invention with an eye piece.

Now referring to FIG. 15, there is shown another example of the invention (200) comprising a body comprising a cap piece (202), an insertion piece (206) and a hand piece (204). On the face (208) of the cap piece (202) are mounted a push-button switch (212) and eye-piece (214). Push-button switch (212) is electrically connected to a DC power source (215) comprising at least one battery (217) and then to at least one LED lamp light source (218) (see also FIG. 13 Item (126)) located adjacent to the second end (220) of the insertion piece (206) and beneath the portion (221). The light source may also be located in the hand piece (204) and provides illumination by way of a light guide (fiberoptic bundles) that travels through the bore (224) and terminate at the distal end of the device (218) (at the second end (220) of the insertion piece (206) and beneath the portion (221)). The push-button switch controls the on-off function of the illumination system. The illumination system provides lighting to support the image viewing system and may include but is not limited to the use of incandescent or LED lamps.

The illumination system provides a bright light source sufficient to illuminate the interior of the throat and path to and including the vocal cords and surrounding anatomy during intubation. Electrical wiring (222) for the illumination system is contained within a bore (224) that runs the length of the insertion piece (206) in order to connect at least one battery (217) to the lamp(s). Alternatively when the lamp is located within the hand piece, light transmission occurs by way of fiber optic bundles that travel within the bore (224) to the distal end (218) of the device.

Figure 13:
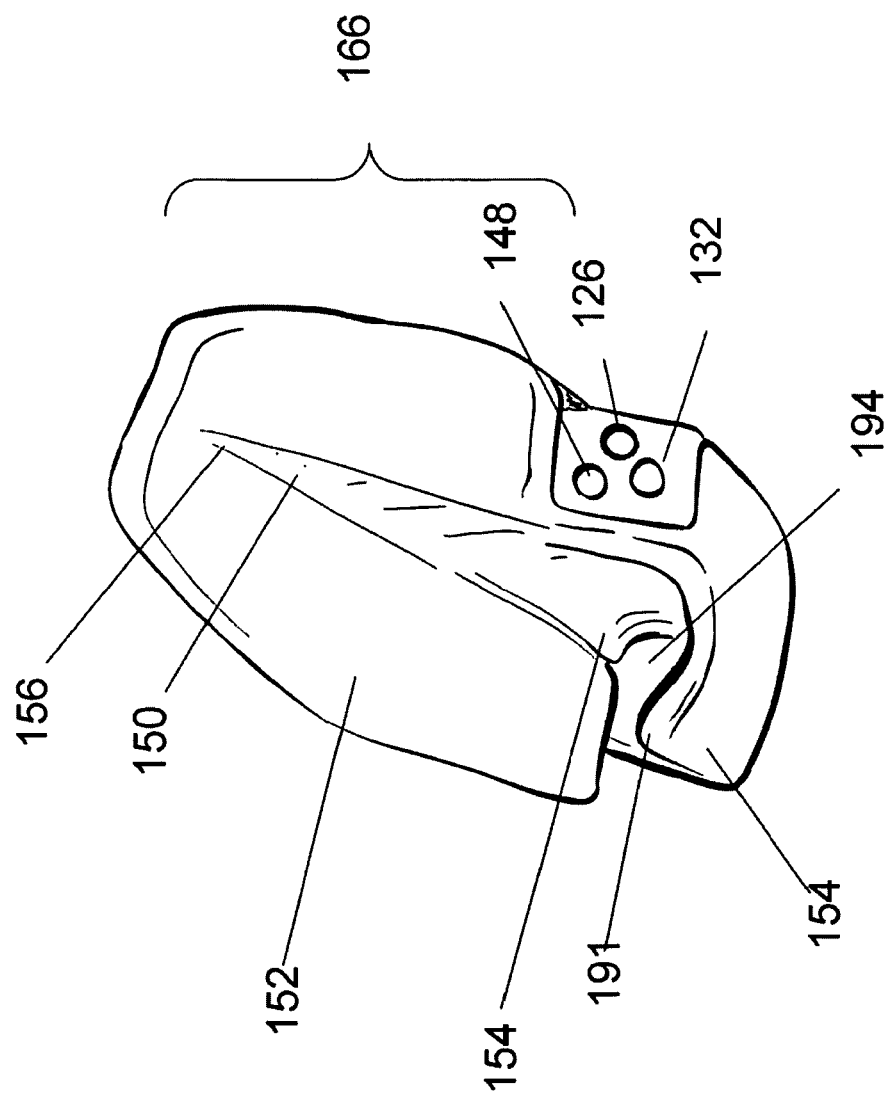
FIG. 13 is an enlarged view of the exit portal of the channel of one example of the invention.

The eye-piece (214) is optically connected to the distal image gathering component (216) (See also FIG. 13 Item (148)) located adjacent to the distal illumination component portal (218) by a fiberoptic member (228) that travels through bore (224) with the illumination system components (222). This combination of image gathering and illumination allows the clinician to view safe passage of the endotracheal tube through the vocal cords into the patient's trachea through the eyepiece.

Figure 16:
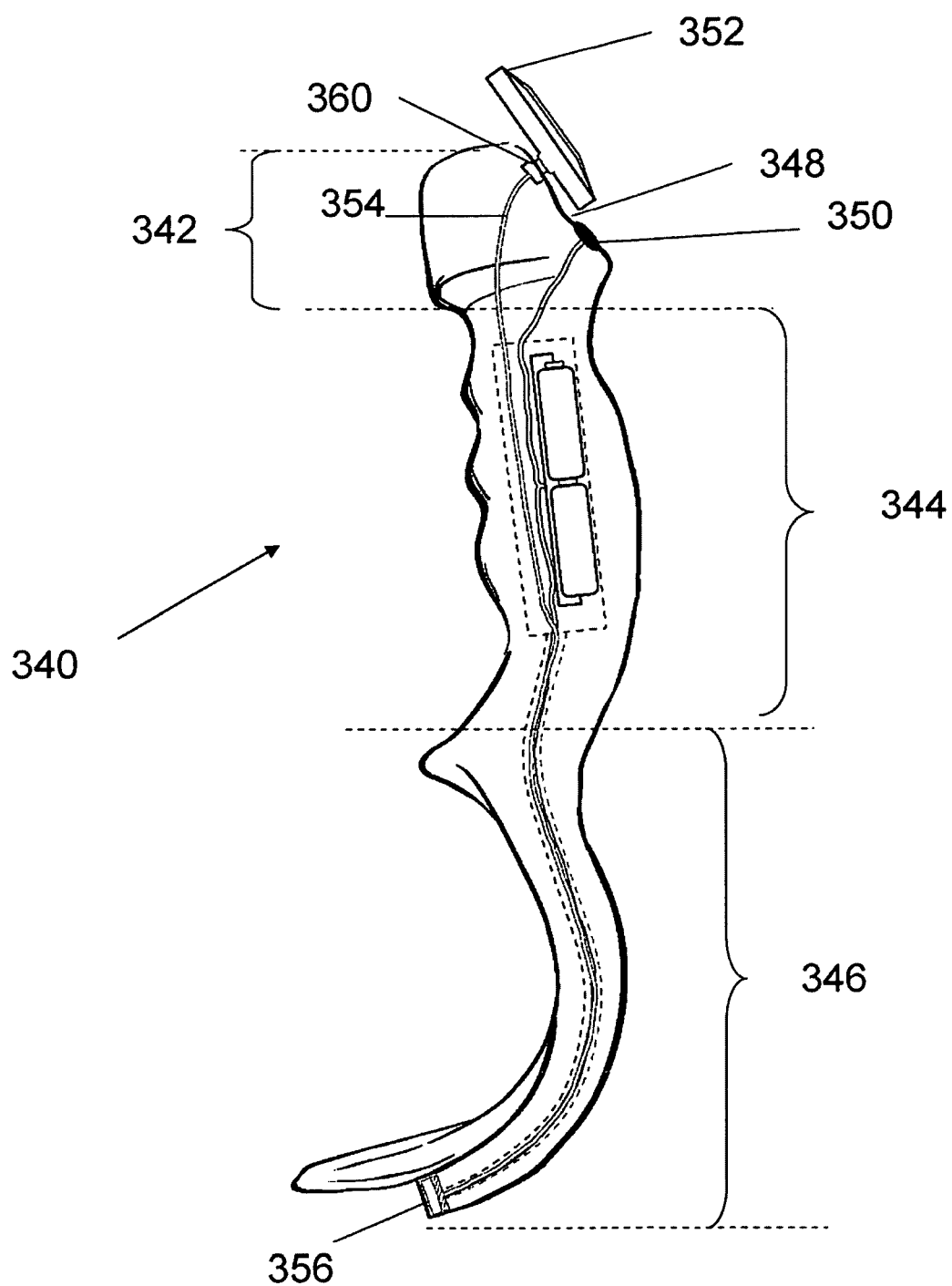
FIG. 16 illustrates a side view of another example of the invention with a video display screen.

Referring to FIG. 16 there is shown another example (340) of the invention comprising a cap piece (342), a hand piece (344) and an insertion piece (346). Mounted to the face (348) of the cap piece (342) are push-button switch (350) and video display unit (352). Video display unit (352) is electrically connected (354) to a camera (356) (See also FIG. 13 Item (148)) located adjacent to the light sources. In another example of the device the video display (352) is removable from the top cap for placement in a convenient location during intubation and connected to the camera wirelessly or by means of an extension cord that can be inserted into plug (360). The video display unit is powered by the same source as used to power the illumination system.

Figure 17:
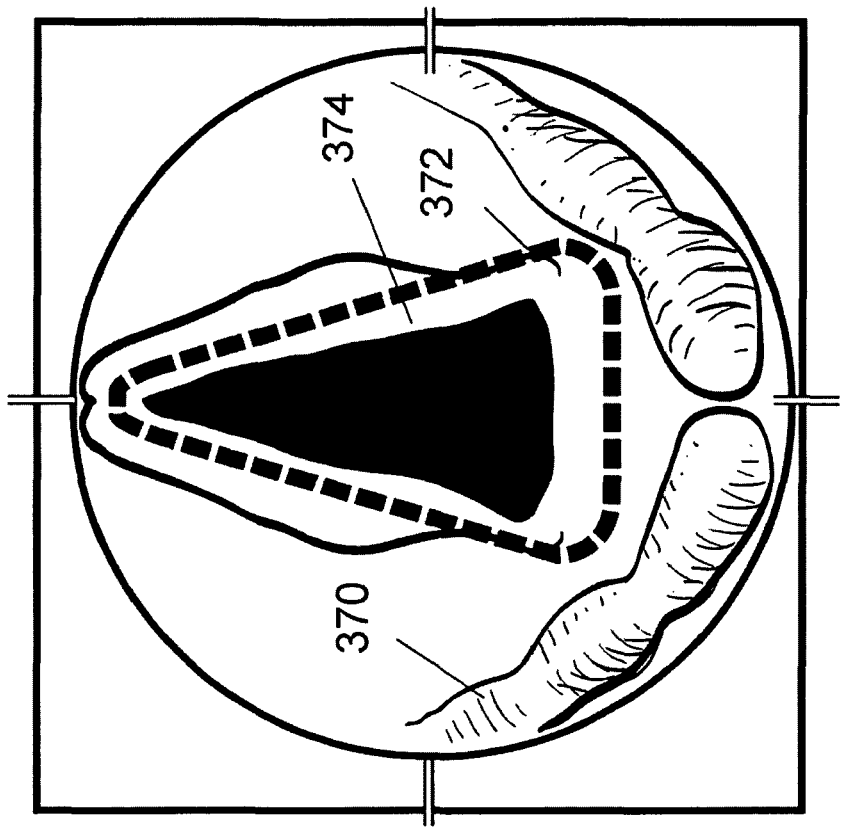
FIG. 17 illustrates the aiming reticle of one example of the invention.

Referring to FIG. 17 there is illustrated a representation of what might be seen on the display (352). The vocal cords (374) should be seen clearly when the insertion piece is inserted and then lifted vertically to manipulate the epiglottis and expose the vocal cords. An aiming reticle (372) that mimics the shape of the inlet between the vocal cords is provided as an aid to the novice user in aligning the insertion piece tip on the vocal cords, both on a left-right and up-down basis, to achieve a smooth and successful intubation. Once aligned the user can insert the endotracheal tube through the insertion piece and can view it passing between the vocal cords and therefore entering the trachea.

Now referring to FIGS. 18 and 19 there is illustrated one advantage of the invention (FIG. 19) when compared to a prior art device (FIG. 18).

In FIGS. 18 and 19 the vocal cords are shown with wide separation for illustrative purposes. Clinically, they are much closer together. In addition this view is from below the cords looking up and therefore the right vocal cord (402) appears on the left side of the FIGS. 18 and 19 and correspondingly the left vocal cord (404) appears on the right side of the FIGS. 18 and 19. Returning to the key challenge of delivering the endotracheal tube with a beveled tip safely between the vocal cords, it is necessary to view FIG. 18. FIG. 18 shows the bottom view of the portion (166) with the tube (400) inserted partially through the exit portal (194) of the insertion device. The tip (170) of the second linear portion (166) is usually below the epiglottis, close to the vocal cords (cross-sectionally represented by circles (402) and (404)) and the tube is poised to pass between then. The image gathering component (406) may have a focal path (408) that is typically focused on the center (410) of the blade tip (170). As the clinician aligns the tip (170) to centre between the vocal cords the endotracheal tube tip (400) may therefore follow a path that may result in contact with the right vocal cord (402) as shown by arrow (412) potentially preventing tube passage and damaging the vocal cord. This problem becomes more severe if the vocal cords are closer together, as may be the case in some patients requiring emergency intubation.

Our invention acknowledges the fact that an endotracheal tube has its leading edge beveled as illustrated in FIGS. 18 and 19. Therefore, the right leading edge extends further forward than the left. This is to aid passage of the tube during direct laryngoscopy. However, when passing a tube using scopes of the type of our invention the right leading edge of the tube can catch and hold up on the right vocal fold, thus impeding forward tube passage down the trachea. In this example of our invention the lens of the imaging gathering component (406) is designed so that it aims a little to the right of midline. This will result in the image of the vocal cords lying to the left of midline. The clinician would then, in the effort to center the view of the cords in the midline, naturally twist the scope very slightly to the left. This would, in turn, result in the right leading edge of the tube, as it was advanced, being kept away from the right vocal fold. In another example of the invention, the same result can be obtained by having the entire delivery channel proceed very slightly from right to left as it passes down within the insertion piece.

Referring now to FIG. 19 this example of the invention relies upon an image gathering system (420) with an improved focal path (422) that is angled slightly right of midline and closer to the right vocal cord (402). The slight eccentricity in the focal path will result in an optical view of the cords offset to the left, which prompts the clinician to twist the tip (170) of the second linear portion (166) slightly to the left to center the cords in the visual field thereby helping avoid right vocal cord contact as the tube is advanced, as illustrated by arrow (424). It can be appreciated that the image gathering system (420) can be moved to the other side of the exit portal (194) blade with the same desired effect of alignment between the tube tip and the vocal cords.

Figure 19A:
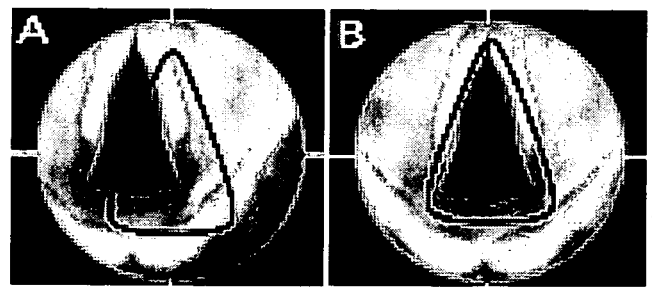
FIG. 19A illustrates the aiming reticle in use.

Now referring to FIG. 19A.

Photo A and Photo B illustrate the advantage of using a video display unit with the aiming reticle as shown in FIG. 19 to ensure appropriate device aiming for easy tube passage into the trachea. Once correctly aligned with the vocal cords, as in Photo B, tube passage should be non-problematic.

Figure 20:
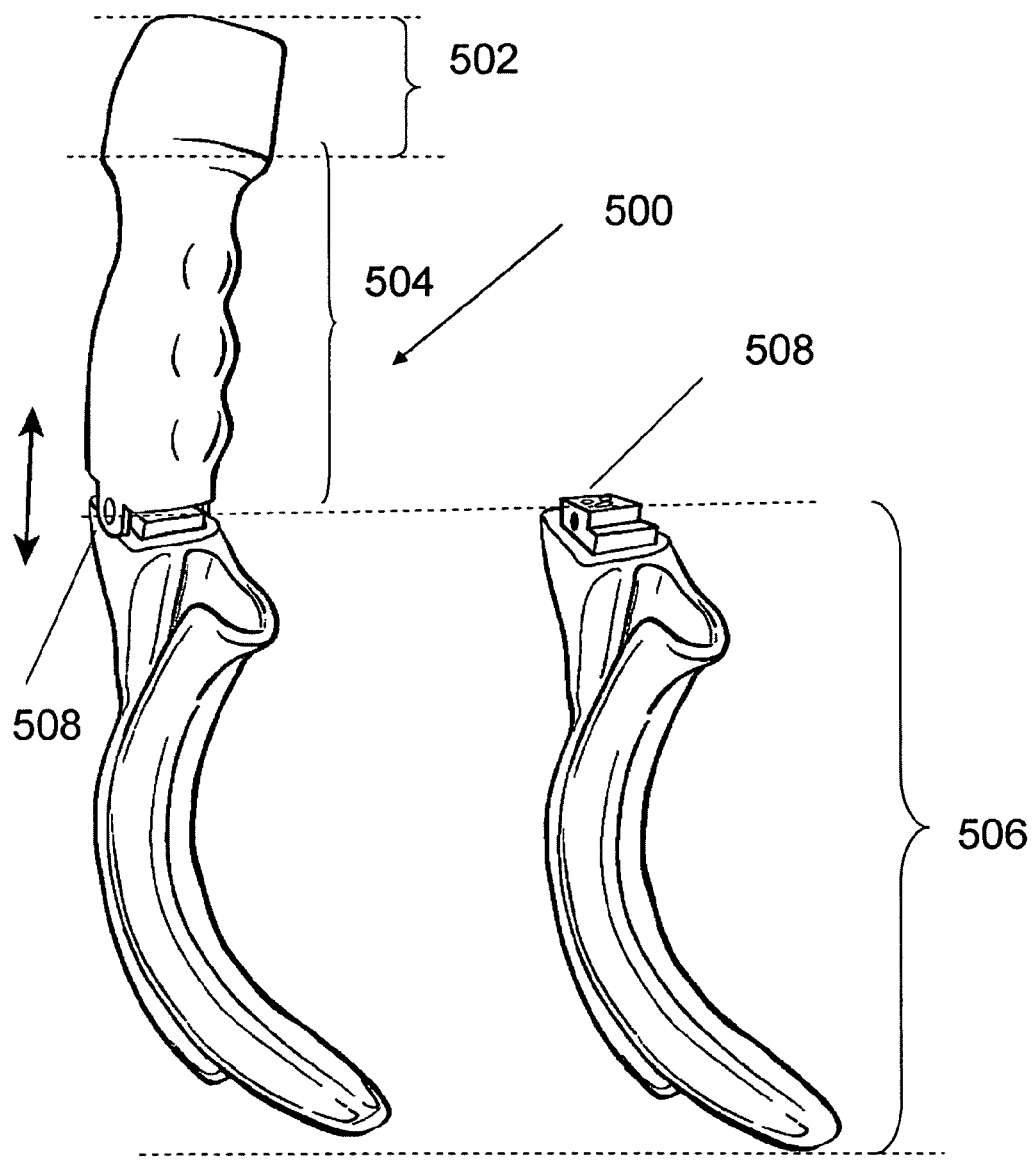
FIG. 20 illustrates another example of the invention with removable insertion pieces.

Now referring to FIG. 20, there is shown another example of the invention (500) comprising a body comprising a cap piece (502), a hand piece (504) and an insertion piece (506). In this example, insertion piece (506) is separable from hand piece (504) by joining means (508). In this example, the insertion piece can be removed for disposal or sterilized for repeated uses. As well, the separable hand piece and insertion piece permits use of varying component sizes to accommodate patients of varying size. The joining means is adapted to permit electrical and optical connections from the insertion piece into the hand piece so that all of the previously described examples of the invention can be accommodated with this design.

Although the description above contains much specificity, these should not be construed as limiting the scope of the invention but as merely providing illustrations of some of the presently preferred embodiments of this invention. Thus the scope of the invention should be determined by the appended claims and their legal equivalents.

What is claimed is:

1. In an airway intubation device comprising:
   (a) a cap piece having a face;
   (b) an ergonomically adapted hand piece for housing a power source;
   (c) a linear-curved-linear insertion piece having a truncated tip having a centre point, an endotracheal tube delivery channel having a first end for receiving said endotracheal tube and a second end for deployment of the endotracheal tube into a patient's trachea, said channel disposed within one side of said linear-curved-linear insertion piece, and a bore within the linear-curved-linear insertion piece, said bore having a distal end;
   (d) the improvement comprising the combination of:
      (i) a system for generating a video signal for video imaging the insertion of the endotracheal tube into said patient's trachea and between said patient's vocal cords, wherein said system comprises a camera and at least one LED lamp disposed adjacent to said distal end of the bore, wherein said system is electrically connected through the bore to said power source;
      (ii) a video display unit for receiving said video signal from the system, said video display unit operable when coupled to and detached from said device so that a clinician can view said video imaging;
      (iii) wherein when said video display unit is detached from the device it remains either cable coupled or wirelessly coupled to the system to receive the video signal;
      (iv) an aiming system comprising:
         (1) an anatomically correct aiming reticle disposed over the video imaging and mimicking the patient's vocal cords so that during intubation the clinician is able to align the patient's vocal cords with said anatomically correct aiming reticle and guide the endotracheal tube between the patient's vocal cords without contact; and,
         (2) a focal path of said camera disposed a predetermined amount to the right of said centre point resulting in a leftward shift of the video imaging said predetermined amount thereby avoiding right vocal cord contact.

\* \* \* \* \*